United States Patent [19]

Löhn

[11] 4,177,024
[45] Dec. 4, 1979

[54] VANE AIR MOTOR WITH ECCENTRIC ADJUSTMENT RING AND BEARING RING FOR VANE ENDS

[75] Inventor: Gerd Löhn, Biberach, Fed. Rep. of Germany

[73] Assignee: Kaltenbach & Voigt GmbH & Co., Biberach an der Riss, Fed. Rep. of Germany

[21] Appl. No.: 794,227

[22] Filed: May 5, 1977

[30] Foreign Application Priority Data

May 14, 1976 [DE] Fed. Rep. of Germany ....... 2621485

[51] Int. Cl.² ................... F01C 1/00; F01C 21/16;
F16C 35/00; F16C 35/04
[52] U.S. Cl. ........................ 418/16; 418/173;
418/270; 308/9
[58] Field of Search ............ 418/16, 23, 30, 270,
418/173; 308/DIG. 1, 9

[56] References Cited

U.S. PATENT DOCUMENTS

| 860,628 | 7/1907 | Boone | 418/268 |
|---|---|---|---|
| 953,539 | 3/1910 | Mendizabal | 418/16 |
| 2,302,411 | 11/1942 | Behrens | 418/16 |
| 2,324,903 | 7/1943 | Beckman | 418/173 |
| 2,575,524 | 11/1951 | Mitchell | 418/270 |
| 2,590,729 | 3/1952 | Scognamillo | 418/173 |
| 2,612,110 | 9/1952 | Delegard | 418/16 |
| 2,777,543 | 1/1957 | O'Connor | 418/16 |
| 3,210,848 | 10/1965 | Bizzigotti | 308/9 |
| 3,306,375 | 2/1967 | Macks | 308/9 |
| 3,539,281 | 11/1970 | Kramer | 418/173 |

FOREIGN PATENT DOCUMENTS

454548 2/1949 Canada .................................... 418/16

*Primary Examiner*—John J. Vrablik
*Attorney, Agent, or Firm*—Haseltine, Lake & Waters

[57] ABSTRACT

A pneumatically operated vane-type motor for driving medical or dental handpieces. A housing forms a rotor chamber in which a rotor is mounted, the rotor having axial slots in which radially moveable vanes are housed. An adjustment ring is positioned between the inner surface of the housing and the outer ends of the vanes, and is moveable to adjust the speed and torque characteristics of the rotor without requiring adjustment in the compressed air supply. To this end, the adjustment ring has a cylindrical outer surface engaging the inner surface of the housing, and a cylindrical inner surface towards which the vanes extend. The axes of the inner and outer surfaces of the adjustment ring are spaced-apart.

15 Claims, 6 Drawing Figures

VANE AIR MOTOR WITH ECCENTRIC ADJUSTMENT RING AND BEARING RING FOR VANE ENDS

FIELD OF THE INVENTION

This invention related to a vane-type motor operable by compressed air and comprising a sleeve-like housing having a cylindrical inner surface which is circular in cross-section and which forms a stator, said stator forming a rotor chamber; a rotor mounted for rotation in said rotor chamber about an axis which extends parallel to the axis of said inner surface; axially extending slots provided in said rotor; rotor vanes radially moveably mounted in said slots and extending with their radially outer ends towards said inner surface of the housing; and air inlet means and air outlet means communicating with said rotor chamber.

When compressed air is admitted to the motor, it passes through the air inlet means into the rotor chamber to move the nearest vane of the rotor, so that the rotor commences to rotate and the next vane is acted on by the compressed air. The speed of the vane-type motor may be, for example, about 20,000 to 100,000 r.p.m.

DESCRIPTION OF THE PRIOR ART

A motor of the above type is disclosed in German Offenlegungsschrift No. 2 304 666. In such motors, output control is possible only by variation of the supply of compressed air. For example, when the compressed-air supply is throttled, the speed and the torque are reduced. This simultaneous reduction of speed and torque is disadvantageous and often undesired. Although, on throttling of the compressed-air supply and hence reduction of the speed, it is possible to lessen the simultaneous and inevitable reduction of the torque by means of gears or valve arrangements associated with the motor which increase the supply of compressed air on loading of the motor—by means of the dynamic pressure coming into play in the compressed-air supply duct leading to the air inlet aperture of the motor—, the gears and valve arrangements necessary for this purpose are complex, costly and susceptible to breakdown. Moreover, in the case of valve arrangements, these are not capable of responding rapidly enough. The same applies to air turbines of the kind known with dental handpieces, for example according to German Offenlegungsschrift No. 1 935 342.

It is an object of the invention to provide a pneumatic vane-type motor wherein a stepless speed regulation is possible by virtue of the fact that substantially the same torque is established in the upper speed ranges of about 150,000 to 400,000 r.p.m., and the torque even increases in the lower speed ranges from about 20,000 to 150,000 r.p.m.

SUMMARY OF THE INVENTION

According to the invention there is provided a vane-type motor operable by compressed air and comprising;

a sleeve-like housing having a cylindrical inner surface which is circular in cross-section and which forms a stator, said stator forming a rotor chamber; a rotor mounted for rotation in said rotor chamber about an axis which extends parallel to the axis of said inner surface;

axially extending slots provided in said rotor;

rotor vanes radially moveably mounted in said slots and extending with their radially outer ends towards said inner surface of the housing;

air inlet means communicating with said rotor chamber for supplying compressed air to drive the rotor;

air outlet means communicating with said rotor chamber;

an adjustment ring positioned between said inner surface of the housing and said outer ends of the vanes, said ring being rotatable relative to said inner surface of the housing;

a cylindrical outer surface provided on said adjustment ring which engages said inner surface of the housing;

and a cylindrical inner surface provided on said adjustment ring and towards which the vanes extend, the inner and outer surfaces of said adjustment ring being circular in cross-section and having axes which are spaced from each other.

The adjustment ring can be turned with a smooth movement in relation to the inner surface of the housing in such manner that the axis of the inner surface of the ring coincides with the axis of the rotor. In this position, the motor has a speed Z2 and a torque M1. When the adjustment ring is turned, so that the axis of its inner surface moves away from the axis of the rotor, until finally the rotor comes into contact, or almost into contact, with the inner surface of the adjustment ring, the speed falls to a value Z1, but at the same time the torque increases to a value M2. Hence, with a constant compressed-air supply, a speed reduction can be effected with a simultaneous increase in the torque without any gearing or valve arrangement being necessary for this purpose. Moreover, the cost is very low owing to the introduction of the simple adjustment ring.

The speed range of the proposed vane-type motor may surprisingly be enlarged without any loss of torque by providing the rotor with turbine blades. When the adjustment ring is so set that the axis of its inner surface coincides with the axis of the rotor, the motor has a speed Z2+ which is higher than the aforesaid value Z2, and a torque M1+ which is higher than the aforesaid value M1. In this position, the turbine blades effect a readier and more rapid starting of the vanes and the aforesaid increase of the speed. When the adjustment ring is turned, so that the axis of its inner surface moves away from the axis of the rotor, until finally the rotor comes into contact, or almost into contact, with the inner surface of the adjustment ring, the speed falls to a value Z1+, the torque simultaneously increasing to a value M2+. The speed Z1+ is higher than the value Z1 and the torque M2+ is higher than the value M2.

The effectiveness of the arrangement may be further enhanced if the slots which receive the vanes are situated in the turbine blades.

In order to ensure reliable starting of the rotor, it is proposed that the air inlet means be situated in one end wall of the housing and that the air outlet means be situated in the other end wall of the housing, the said inlet and outlet means being staggered in relation to one another.

If a special air inlet aperture is not provided for the admission of air to the turbine blades, it is desirable for the turbine blades to have a surface section on which there can act the compressed-air stream coming from the air inlet aperture or apertures situated in one end wall of the housing.

For the rotation of the adjustment ring rhough 180° in relation to the inner surface of the housing, there may be provided on one end wall of the latter a rotatable control button which is in engagement with the adjustment ring by means of a driving pin extending through an elongate hole in the end wall. For the same purpose, the housing may be formed with a lateral peripherally extending elongate hole for the passage of a radial adjustment pin on the adjustment ring.

The aforesaid speed and torque values which can be obtained by rotation of the adjustment ring may be further increased if there is provided between the inner surface of the adjustment ring and the outer ends of the vanes a bearing ring which is coaxial with the aforesaid inner wall and freely rotatable in relation thereto and against which the vanes lie at their outer ends.

By virtue of the fact that the outer ends of the vanes in this alternative construction are not in contact with the inner surface of the adjustment ring which is fast with the housing in its set position, but are in contact with the freely rotatable bearing ring, the outer ends of the vanes do not undergo any sliding friction. Owing to the completely harmless static friction of the outer ends of the vanes on the inside surface of the bearing ring, the latter is driven during the rotation of the rotor. Due to the fact that the outer ends bear firmly against the bearing ring in a harmless manner, no leakage air is lost, whereby a higher speed and a higher torque, and hence a higher output of the motor are obtained with long useful life. The motor is further distinguished by smooth, vibration-free running owing to the elimination of the sliding friction between the outer ends and the inner surface of the adjustment ring.

The vanes may be held in engagement with the bearing ring in a conventional manner, for example by centrifugal force, by springs disposed in the longitudinal slots of the rotor or by compressed air introduced into the longitudinal slots.

The bearing ring may be slideably mounted on the inner surface of the adjustment ring. However, in order here again to avoid sliding friction, the bearing ring may be mounted on the inner surface of the adjustment ring by means of rolling bodies, for example balls. In order to avoid attendant rolling noises, there may be provided between the bearing ring and the inner surface of the adjustment ring a ring-shaped gap to which compressed air can be admitted to form an air bearing for the bearing ring. Such an air bearing has the further advantage that a completely vibration-free running of the rotor and of the air bearing is ensured.

In the case of such an air bearing, either the bearing ring may be formed with at least one passage for the supply of compressed air to the ring-shaped gap from the space between the rotor and the bearing ring, or the adjustment ring may be formed with at least one outlet aperture for supplying compressed air to the ring-shaped gap from outside the motor.

More particularly in the case where the vanes are held in engagement with the bearing ring by centrifugal force, a good driving of the bearing ring by the vanes is obtained even in the starting condition in which the contact with the bearing ring is still relatively loose, by forming the inner surface of the bearing ring with axial grooves for receiving the outer ends of the vanes.

DESCRIPTION OF THE PREFERRED EMBODIMENTS

The illustrated pneumatic vane-type motor consists of a sleeve-form housing 1 which has a cylindrical inner wall 2 of circular cross-section and which forms the stator. The housing 1 may be surrounded by an outer casing 3 having the form of a circular cross-section cylinder. Situated within the housing 1 is a rotor 4 which is mounted in accordance with FIGS. 1 and 2 in end housing covers 5, 6 by means of ball bearings 7, 8. For reasons of manufacture, the axis of rotation D of the rotor 4 coincides with the axis of the external casing 3, for example in accordance with FIGS. 1 and 3. In any case, however, the axis of rotation D of the rotor 4 extends parallel with the axis A of the circular cylindrical inner wall 2, for example in accordance with FIGS. 3 and 4, and is offset from the said inner wall.

Mounted in longitudinal slots 9 in the rotor 4 in such manner as to be radially movable are vanes or laminations 10 whose outer ends 11 extend towards the circular cylindrical inner wall 2.

There open into the space 12 between the rotor 4 and the circular cylindrical inner wall 2 of the housing 1 three apertures 13, 14, 15 (FIG. 4) which have an angular spacing of about 120°. When compressed air is admitted to the aperture 13 and the latter consequently acts as an air inlet aperture, the apertures 14, 15 are air outlet apertures. On the other hand, when compressed air is admitted to the aperture 14, and the latter thus acts as an air inlet aperture, the apertures 13, 15 are air outlet apertures. Consequently, the aperture 15 is always an air outlet aperture.

Figure 3:
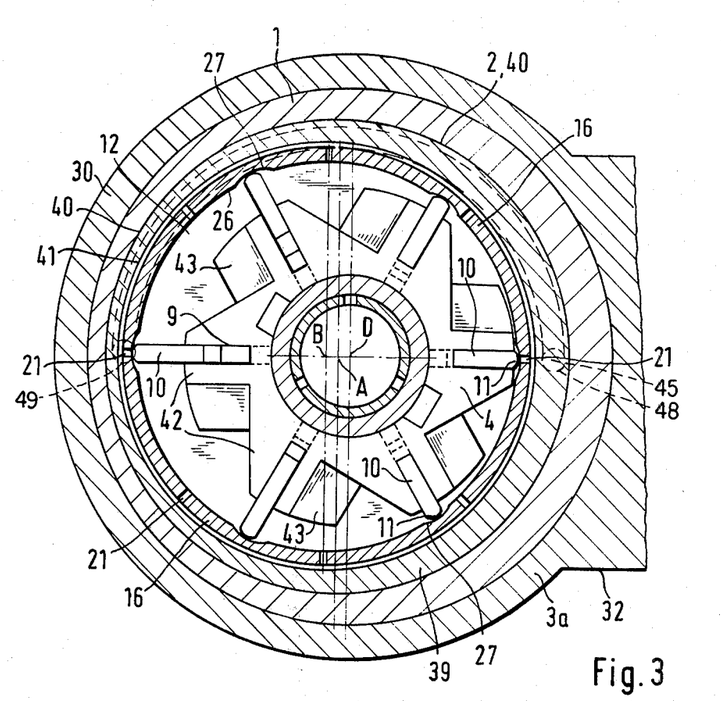
FIG. 3 illustrates the motor in section along the line III—III of FIG. 2.

Situated between the circular cylindrical inner wall 2 of the housing 1 and the outer end 11 of the laminations 10 is an adjustment ring 39 which is rotatable in relation to the inner wall 2 and is in contact with the latter, and towards which the outer ends 11 of the vanes 10 extend. The axis of the circular cylindrical external wall 40 of the adjustment ring 39, which coincides with the axis A of the circular cylindrical inner wall 2 of the housing 1, and the axis B of the circular cylindrical inner wall 41 of the adjustment ring 39 are offset from one another, for example as illustrated in FIG. 3. In the embodiment illustrated in FIG. 4, the rotor 4 has a circular cross-section. In the other embodiments, the rotor 4 is provided with turbine blades 42, the longitudinal slots 9 which receive the vanes 10 being situated in the turbine blades 42.

Figure 2:
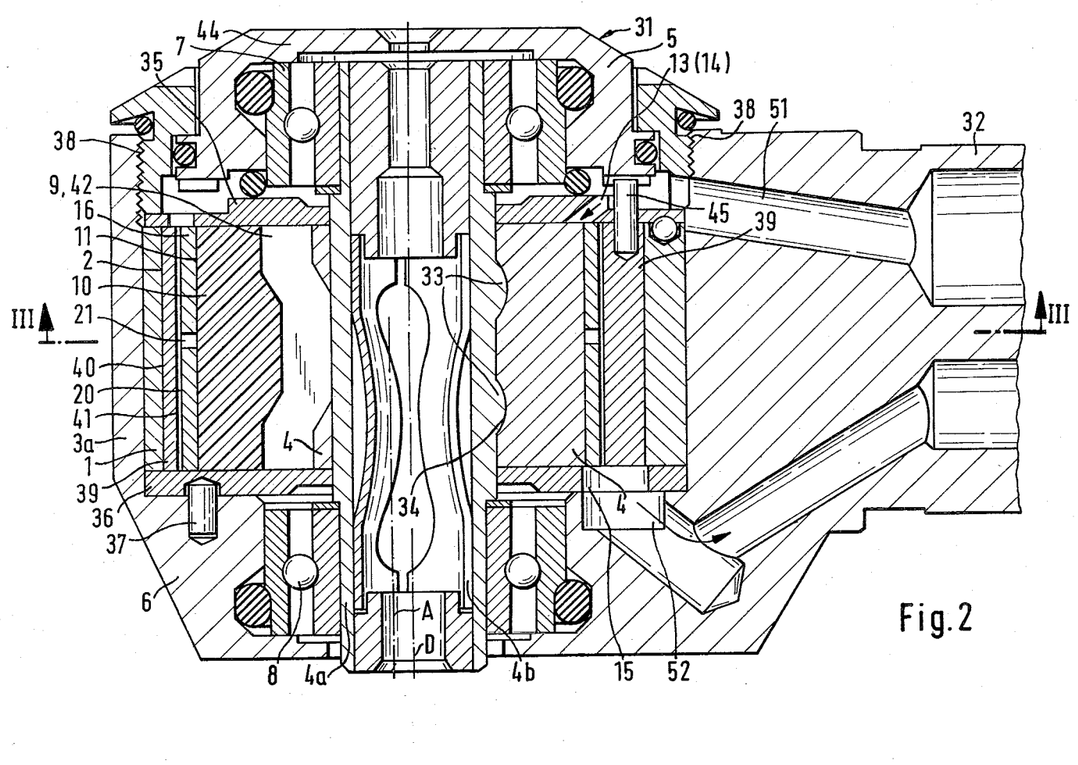
FIG. 2 illustrates in longitudinal section a pneumatic vane-type motor which is suitable, for example, for a dental handpiece whose head extends at an angle.
Figure 4:
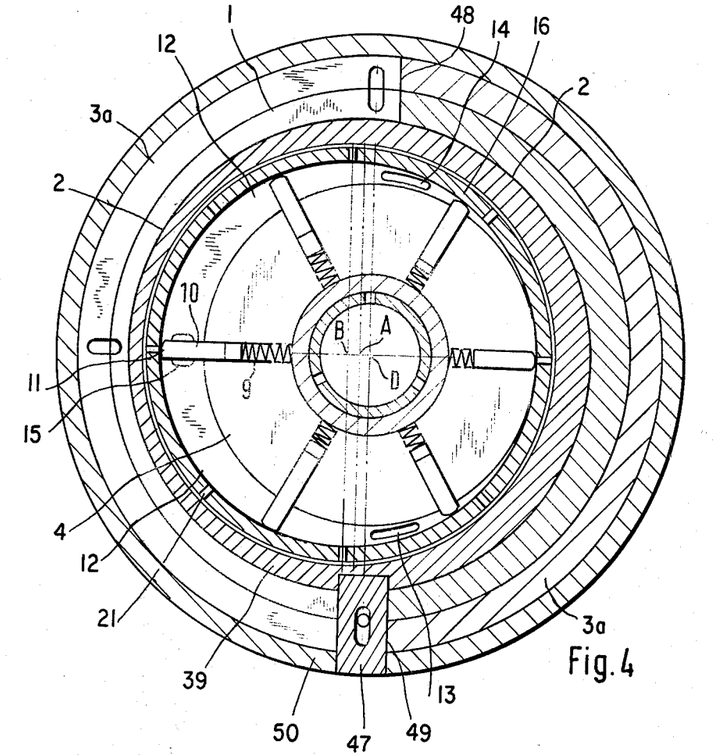
FIG. 4 illustrates a sectional view taken along line line IV—IV in FIG. 1.
Figure 5:
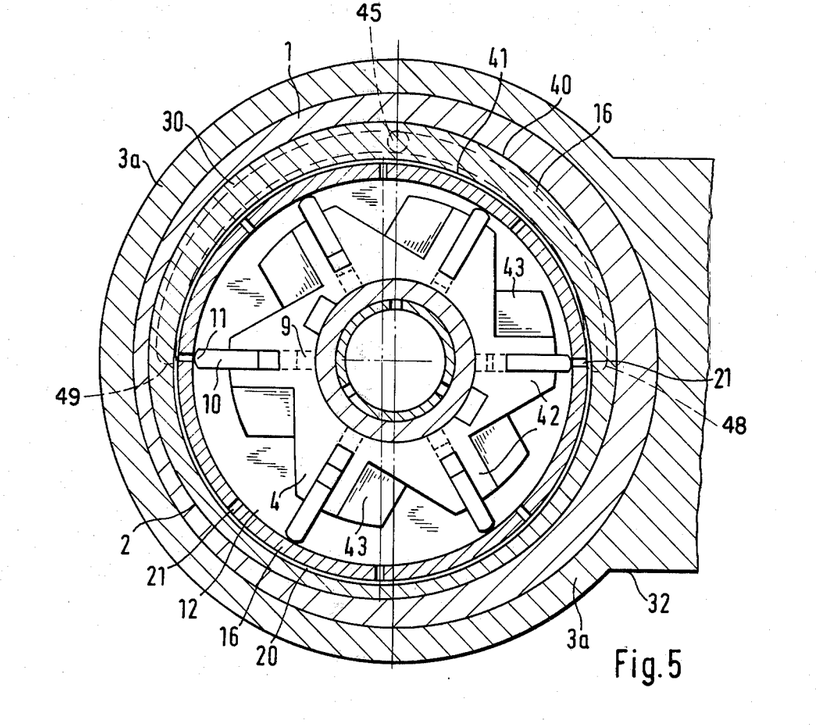
FIG. 5 illustrates the motor according to FIG. 3 in a modified position.
Figure 6:
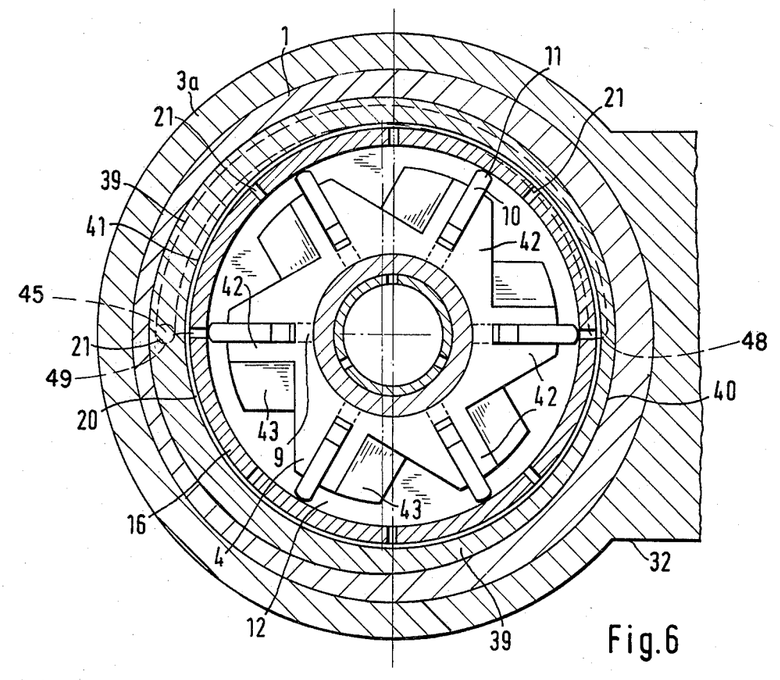
FIG. 6 illustrates the motor according to FIGS. 3 and 5 in a further modified position.

In the embodiment illustrated in FIG. 2, the air inlet apertures 13 (14) are situated in one end wall 35 and the air outlet aperture 15 is situated in the other end wall 36 of the housing 1, the inlet and outlet apertures being offset from one another as shown in FIG. 4. The turbine blades 42 have a surface section 43 which can be acted-on by the compressed-air stream coming from the air inlet aperture or apertures 13 (14) situated in one end wall 35 of the housing 1.

Disposed on one end wall 35 of the housing 1 as shown in FIG. 2 is a rotatable operating button 44, which is in engagement with the adjustment ring 39 by means of a driving pin 45 extending through an elongate hole in the end wall 35.

Figure 1:
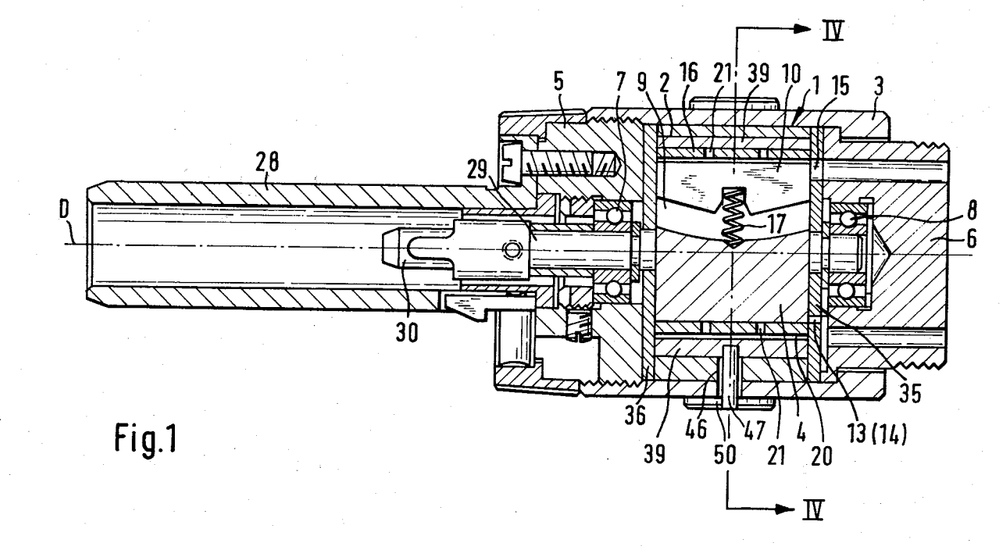
FIG. 1 illustrates in longitudinal section a pneumatic vane-type motor suitable, for example, for a straight dental handpiece.

In the other embodiments, the external casing 3 and the housing 1 are provided with a lateral peripherally extending elongate hole 46 for the passage of a radial adjustment pin 47 of the adjustment ring 39, for example as shown in FIG. 1.

Both the operating button 44 and the adjustment pin 47 are accessible from the outside and can be readily manually adjusted. The aforesaid elongate holes extend over an arc of 180°, as is apparent from the stops 48, 49 of the elongate hole in FIGS. 3 to 6. In accordance with FIG. 1, the adjustment pin 47 is provided with an operating ring 50 surrounding the external casing 3.

In the position illustrated in FIG. 4, the vane-type motor can operate at a speed Z1 and with a torque M2. In the position illustrated in FIG. 3, the motor can operate at a speed Z1+ and with a torque M1+. In the position illustrated in FIG. 5, the speed and the torque of the motor have values between Z2+, M1+ (FIG. 6) and Z1+, M2+ (FIG. 3).

The aforesaid speed and torque values may be increased whenever, as shown in FIGS. 1, 2, 3, 5 and 6, there is provided between the circular cylindrical inner wall 41 of the adjustment ring 39 (FIG. 3) and the outer ends 11 of the vanes 10 a bearing ring 16 which is coaxial with the inner wall 41 and freely rotatable in relation thereto, and against which the outer ends 11 of the vanes 10 bear under the action of compression springs 17 (FIG. 1) disposed in the longitudinal slots 9 in the rotor 4, under the action of centrifugal force during the rotation of the rotor (FIGS. 2 to 6).

Situated between the bearing ring 16 and the circular cylindrical inner wall 41 of the adjustment ring 39 is a ring-shaped gap 20 to which compressed air can be admitted to form an air bearing for the bearing ring 16. The latter is formed with a number of passages 21 for the supply of compressed air to the ring-shaped gap 20 from the space 12 between the rotor 4 and the bearing ring 16.

In the embodiment illustrated in FIG. 3, the inner wall 26 of the bearing 16 is formed with axial grooves 27 to receive the outer ends 11 of the vanes 10.

The motor shown in FIG. 1 may be used for attachment to or incorporation in a straight surgical or dental handpiece. For this purpose, a coupling sleeve 28 is provided for connection to the handpiece (not shown). The extended shaft 29 of the rotor 4 is provided with a driving member 30 for that end of the handpiece shaft (also not shown) which is to be coupled.

In the embodiments illustrated in FIGS. 2 to 6, the motor is fitted into the head housing 3a of, for example, a dental angle piece having a bent-over head 31 (FIG. 2). The stem of the head 31 is denoted by 32.

In the embodiment illustrated in FIG. 2, the rotor 4 is formed in two parts. Thus, the rotor 4 also has a separate inner sleeve 4a with an inserted collet 4b for receiving the stem of a tool (not shown), for example of a drill. For a better force-transmitting connection to the actual rotor 4 and for axial securement the inner sleeve 4a is provided with external bosses 33 engaging in corresponding recesses 34 in the inner wall of the actual rotor 4. In this way, the rotor 4 is prevented from running on to limiting discs or end walls 35, 36 provided adjacent the housing covers 5, 6. As shown in FIG. 2, the housing cover 5 is screwed to the head housing 3 by means of a screwthread 38. The lower housing cover 6 as illustrated in FIG. 2 forms with the head housing 3a an integral component unit.

As shown in FIG. 2, the end wall 36 is securely held to the housing cover 6 by means of a fixing pin 37.

In the embodiment illustrated in FIG. 2, the air inlet aperture 13(14) receives compressed air through a compressed-air supply duct 51. The waste air is discharged from the air inlet aperture 15 through an air discharge duct 52.

As is apparent from FIGS. 3 to 6, the housing 1 has circular cross-section cylindrical outer wall which is so situated in relation to the circular cylindrical inner wall 2 that, as in the case of the adjustment ring 39, the axis of the circular cylindrical outer wall and the axis of the circular cylindrical inner wall 2 are offset in relation to one another.

Figure 7:
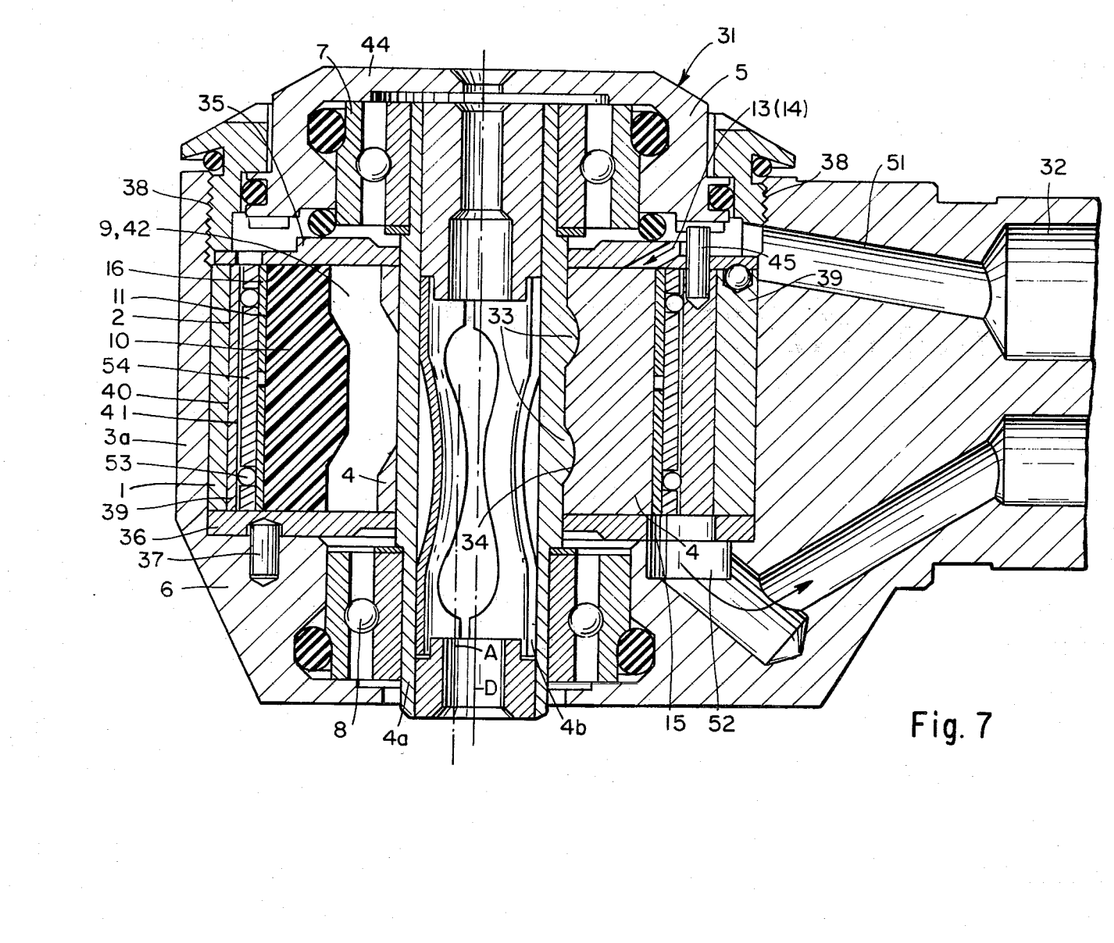
FIG. 7 illustrates an embodiment modified as compared with FIG. 2.

In the embodiment of FIG. 7, the bearing ring 16 is located by means of ball bearings 53 held by a cage or race 54 on the circle cylindrical inside wall 41 of the adjustment ring 39.

I claim:

1. A pneumatic vane-type motor for a dental handpiece to drive a dental tool operable by compressed air and comprising:

a sleeve-like housing having a cylindrical inner surface which is circular in cross-section and which forms a stator, said stator forming a rotor chamber;
a rotor mounted for rotation in said rotor chamber about an axis which extends parallel to the axis of said inner surface;
axially extending slots provided in said rotor;
rotor vanes radially movably mounted in said slots and extending with their radially outer ends towards said inner surface of the housing;
air inlet means communicating with said rotor chamber for supplying compressed air to drive the rotor;
air outlet means communicating with said rotor chamber;
an adjusting ring positioned between said inner surface of the housing and said outer ends of the vanes, said ring being rotatable relative to said inner surface of the housing;
a cylindrical outer surface provided on said adjustment ring which engages said inner surface of the housing;
a cylindrical inner surface provided on said adjustment ring and towards which the vanes extend, the inner and outer surfaces of said adjustment ring being circular in cross-section and having axes which are spaced from each other; and a bearing ring positioned between said inner surface of the adjustment ring and said outer ends of the vanes, said bearing ring being co-axial with and freely rotatable relative to said inner surface of the adjustment ring, and said outer ends of the vanes bearing against said bearing ring.

2. A vane-type motor according to claim 1, including housing end wall partly defining said rotor chamber, a rotatable operating button mounted on said end wall, and a driving pin engaging said button and extending through a hole in said end wall to engage said adjusting ring.

3. A vane-type motor according to claim 1, including a peripherally extending elongate hole formed in said housing, and an adjustment pin connected to said adjustment ring extending through said hole.

4. A vane-type motor according to claim 1, including roller means rotatably mounting said bearing ring on said adjustment ring.

5. A vane-type motor according to claim 1, including an annular clearance gap defined between said inner surface of said adjustment ring and said bearing ring to which compressed air can be admitted to form an air bearing for the bearing ring.

6. A vane-type motor according to claim 1, in which the bearing ring includes axial grooves formed in its inner surface in which the outer ends of the vanes are received.

7. A vane-type motor according to claim 1, wherein said adjustment ring comprises an eccentric ring turnable for changing the eccentricity of the rotor in relation to the housing to control speed while keeping constant flow, motor torque being maximum at low speed and being minimum at high speed, whereby motor direction remains the same in any adjustment of said adjustment ring.

8. A vane-type motor as defined in claim 1, including turbine blades on said rotor; said slots being formed in said blades; said housing including first and second end walls defining said rotor chamber, said inlet means being formed in one of said walls and said outlet means being formed in the other of said walls, said inlet and outlet means being in staggered relation to each other; a surface portion on each turbine blade to be engaged by compressed air supplied by the air inlet means in the respective one of said end walls; a peripherally extending elongated hole formed in said housing, and an adjustment pin connected to said adjustment ring extending through said hole; roller means rotatably mounting said bearing ring on said adjustment ring; an annular clearance gap defined between said inner surface of said adjustment ring and said bearing ring to which compressed air can be admitted to form an air bearing for said bearing ring; said bearing ring being formed with passage means communicating said rotor chamber with said clearance gap; said adjustment ring being formed with passage means communicating with said clearance gap and with the exterior of the motor; said bearing ring including axial grooves formed in its inner surface in which the outer ends of the vanes are received, said adjustment ring comprising an eccentric ring turnable for changing the eccentricity of the rotor in relation to the housing to control speed while keeping constant flow, motor torque being maximum at low speed and being minumum at high speed, whereby motor direction remains the same in an adjustment of said adjustment ring.

9. A vane-type motor according to claim 1 including an annular clearance gap being defined between said inner surface of said adjustment ring and said bearing ring to which compressed air can be admitted to form an air bearing for the bearing ring, said bearing ring being formed with passage means communicating said rotor chamber with said clearance gap.

10. A vane-type motor according to claim 1, wherein said adjustment ring is eccentric to the motor rotor axis and influences the eccentricity of the motor rotor for influencing motor speed, so that motor torque increases with reduction in motor speed, said torque decreasing with increase in motor speed, said adjustment ring being free of openings for passage of pressure medium therethrough, full force of the pressure medium being available for any position of the adjustment ring, the motor speed being adjustable during constant flow of pressure medium.

11. A vane-type motor as defined in claim 1, wherein said adjustment ring is eccentric to the motor rotor axis and influences the eccentricity of the motor rotor for influencing motor speed, so that motor torque increases with reduction in motor speed, said torque decreasing with increase in motor speed, said adjustment ring being free of openings for passage of pressure medium therethrough, full force of the pressure medium being available for any position of the adjustment ring, the motor speed being adjustable during constant flow of pressure medium; a peripherally extending elongated hole formed in said housing, an adjustment pin connected to said adjustment ring extending through said hole; an annular clearance gap being defined between said inner surface of said adjustment ring and said bearing ring to which compressed air can be admitted to form an air bearing for the bearing ring, said bearing ring being formed with passage means communicating said rotor chamber with said clearance; said adjustment ring comprising an eccentric ring turnable for changing the eccentricity of the rotor in relation to the housing to control speed while keeping constant flow, motor torque being maximum at low speed and being minimum at high speed, whereby motor direction remains the same in an adjustment of said adjustment ring.

12. A vane-type motor according to claim 1, including turbine blades provided on the rotor.

13. A vane-type motor according to claim 12, in which said slots are formed in said blades.

14. A vane-type motor according to claim 1, in which the housing includes first and second end walls defining said rotor chamber, said inlet means being formed in one of said walls and said outlet means being formed in the other of said walls, and said inlet and outlet means being in staggered relation to each other.

15. A vane-type motor according to claim 14, including a surface portion provided on each turbine blade to be engaged by compressed air supplied by the air inlet means in the respective one of said end walls.

* * * * *